(12) United States Patent
Kramer et al.

(10) Patent No.: US 7,786,103 B2
(45) Date of Patent: Aug. 31, 2010

(54) METHOD FOR ISOLATING AN INTESTINAL CHOLESTEROL BINDING PROTEIN

(75) Inventors: Werner Kramer, Mainz-Laubenheim (DE); Wendelin Frick, Hunstetten-Beuerbach (DE)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 41 days.

(21) Appl. No.: 11/872,855

(22) Filed: Oct. 16, 2007

(65) Prior Publication Data

US 2008/0167451 A1 Jul. 10, 2008

Related U.S. Application Data

(62) Division of application No. 10/635,008, filed on Aug. 6, 2003, now Pat. No. 7,435,727.

(30) Foreign Application Priority Data

Aug. 6, 2002 (EP) .................. 02017504

(51) Int. Cl.
*A61K 31/397* (2006.01)
*C07K 14/435* (2006.01)
*C07D 205/04* (2006.01)
*C07D 235/02* (2006.01)

(52) U.S. Cl. .................. 514/210.02; 530/350; 540/200; 548/303.7

(58) Field of Classification Search ............ 514/210.02; 530/350; 540/200; 548/303.7
See application file for complete search history.

(56) References Cited

U.S. PATENT DOCUMENTS

| 5,264,372 | A | 11/1993 | Beaumont et al. |
| 5,698,445 | A | 12/1997 | Abo et al. |
| 6,225,454 | B1 | 5/2001 | Miyagi et al. |
| 6,383,734 | B1 | 5/2002 | Marshall et al. |
| 2002/0009714 | A1 | 1/2002 | Altmann et al. |
| 2002/0039774 | A1 | 4/2002 | Kramer et al. |

FOREIGN PATENT DOCUMENTS

| EP | 0245979 | 11/1987 |
| JP | 2000166545 | 6/2000 |
| WO | 90/05147 | 5/1990 |
| WO | 91/18098 | 11/1991 |
| WO | 00/60062 | 10/2000 |
| WO | WO 00/63703 | 10/2000 |
| WO | WO 02/18432 | 3/2002 |

OTHER PUBLICATIONS

Kramer et al., Identification of binding proteins for cholesterol absorption inhibitors as components of the intestinal cholesterol transporter, FEBS Letters, vol. 487, 2000, pp. 293-297.

(Continued)

*Primary Examiner*—Karen Cochrane Carlson
*Assistant Examiner*—Rosanne Kosson (57) ABSTRACT

The invention describes a method for isolating an intestinal protein which is able to bind cholesterol and/or cholesterol uptake inhibitors.

4 Claims, 2 Drawing Sheets

OTHER PUBLICATIONS

Bonnafous et al., Design of Angiotensin II Derivatives Suitable For Indirect Affinity Techniques: Potential Applications to Receptor Studies, J. of Receptor Research, vol. 8, 1988, pp. 295-309.

Crane et al., Reconstitution of Specific Na+-Dependent D-Glucose Transport in Liposomes by Triton X-100 Extrated Proteins From Purified Brush Border Membrantes of Hamster Small Intestine, Biochemical and Biophysical Research Communications, vol. 71, No. 4, 1976, pp. 1010-1015.

Gamble et al., Solubilization of Membrane-Bound Ribonuclease (RNASE) and Alkaline Phosphatase From The Isolated Brush Border of Hymenolepis Diminuta (Cestoda), J. of Parasitology, vol. 66, No. 3, 1980, Abstract.

Hu et al., Lactotransfemin receptor of mouse small-intestinal brush border, Biochem. J., vol. 249, 1988, pp. 435-441.

Kramer et al., Intestinal absorption of dipeptides and Beta-lactam antibiotics II. Purification of the binding protein for dipeptides and Beta-lactam antibiotics from rabbit small intestinal brush border membranes, Biochemica et Biophysica Acta, vol. 1030, 1990, pp. 50-59.

Kurose et al., Cross-linking of a B25 Azidophenylalanine insulin Derivative to the Carboxyl-terminal Region of the alpha-Subunit of the Insulin Receptor, J. of Bio. Chem., vol. 269, No. 46, Nov. 18, 1994, pp. 29190-29197.

Lin et al., The Use of Octyl-Beta-D-Glucoside As Detergent for Hog Kidney Brush Border Membraned, Biochernica et Bicphysica Acta, vol. 557, 1979, pp. 179-187.

Maestracci et al., Proteins and Glycoproteins of the Human Intestinal Brush Border Membane, Biochemica et Biophysica Acta vol. 323, 1973, pp. 113-124.

Mahrouq et al., Photoaffinity Labelling of Brush-Border Membrane Proteins Which Bind Phosphonoformic Acid, J. of Bio. Chem., vol. 256, No. 3, Jan. 25, 1991, pp. 1442-1427.

Mazurier et al., Visualization of lactotransfemin brush-border receptors by ligand blotting, Biochemica et Biophysicia Acta 1985, pp. 453-460.

Weinman et al., Identification of the Human NHE-1 Form of Na+ -H+ Exchanger in Rabbit Renal Brush Border Membranes, J. Clin. Invest., vol. 91, 1993, pp. 2097-2102.

Hasegawa et al., Determination of the Binding Site on the Extracellular Domain of Guanylyl Cyclase C to Heat-stable Enterotoxin, J. of Biol. Chem., vol. 274, No. 44, Oct. 29, 1999, pp. 31713-31718.

METHOD FOR ISOLATING AN INTESTINAL CHOLESTEROL BINDING PROTEIN

This application is a divisional of application Ser. No. 10/635,008, filed Aug. 06, 2003 now U.S. Pat. No. 7,435,727, issued on Oct. 14, 2008, which claims priority to European Application No. EP 02017504.8, filed on Aug. 6, 2002.

The invention refers to a method for isolating an intestinal protein involved in intestinal cholesterol absorption and the ability to bind to cholesterol absorption inhibitors.

In humans, on average about 50% of the cholesterol is present in the lumen of the intestine. The intraluminal cholesterol originates mainly from the diet and from the bile. About 2 g of cholesterol a day is discharged from the bile. The intestinal cholesterol absorption depends greatly on the presence of bile salts. Thus the effect of administration of inhibitors of the reuptake of bile salts or of bile salt sequestrants is to inhibit intestinal cholesterol absorption.

Inhibition of intestinal cholesterol absorption is an important aim of the treatment of lipid disorders, arteriosclerosis and cardiovascular disorders. The prevailing opinion amongst experts is that intestinal cholesterol absorption takes place by physicochemical diffusion.

A number of observations in connection with cholesterol transport which indicate that a protein is involved are known. Intestinal cholesterol absorption is subject to great individual variability. Biochemical data from in vitro experiments indicate that proteins are involved in cholesterol exchange between small unilamellar vesicles and the brush border vesicles of the intestine. It was possible to observe large differences in the intestinal absorption of plant sterols such as β-sitosterol and campesterol, which differ only in a methyl group (β-sitosterol) and an ethyl group (campesterol). In humans, β-sitosterol showed inter alia an inhibition of cholesterol absorption. There are two highly active classes of compounds which inhibit intestinal cholesterol absorption on luminal administration. The compounds are, on the one hand, compounds derived from saponin, such as tiqueside and pamaqueside, and on the other hand certain derivatives of 2-azetidinones. Derivatives of 2-azetidinones as inhibitors of cholesterol absorption are described in Clader et al., J. Med. Chem. 39, 3684-3693, 1996. For the purposes of this invention, absorption is intended to mean attachment of a substance to a protein and transport of this substance with the aid of this protein.

Intestinal absorption of cholesterol significantly contributes to serum cholesterol homeostasis. Inhibitors of intestinal cholesterol absorption like Ezetimibe or Pamaqueside have proven their efficacy as novel cholesterol-lowering agents in clinical trials. Their molecular mode of action as well as the mechanisms of intestinal cholesterol absorption are despite enormous scientific efforts still unknown and discussed controversially. Generally a passive diffusion of cholesterol across plasma membranes and the intestinal brush border cell membrane is assumed, but there is increasing evidence for a protein-mediated process for intestinal cholesterol absorption: Cholesterol absorption shows a strong species difference and structurally closely related plant sterols like β-sitosterol or campesterol with comparable physico-chemical characteristics are in contrast to cholesterol only poorly absorbed making a simple diffusion process unlikely. The existence of specific transport inhibitors for cholesterol, the 2-azetidinones and sterol glycosides, with profound structure-activity-relationships strongly suggest a protein-mediated process for intestinal cholesterol absorption.

Cholesterol is a versatile compound that is vital (in small amounts) to the functioning of the human body. Only animals produce it; no plant product contains cholesterol unless an animal-based product, such as lard, has been added to it in processing. In humans, cholesterol serves three main functions. It is used by certain glands to manufacture steroid or cortisone-like hormones, including sex hormones. It helps the liver to produce bile acids, which are essential to the digestion of fats. Last but not least, it is a main component of cell membranes and structures, a kind of building block for bodily tissues. Without cholesterol, mammalian life would not exist.

The problem with cholesterol arises when the body has too much of it, or has deposits of it in the wrong places. Coronary heat disease results when cholesterol is deposited inside the walls of the heart's coronary arteries, the main suppliers of oxygen to the heart's own muscle tissue. There it contributes to the formation of fatty, toughened blockages called plaque. This buildup of plaque is variously called arteriosclerosis, hardening of the arteries, and arteriosclerosis. Cholesterol can also be deposited within arteries elsewhere in the body, where it may contribute to the occurrence of stroke (from blocked arteries in the brain) and peripheral vascular disease (from arterial blockage in the legs).

In order to travel throughout the body, cholesterol must be packaged in special molecules called lipoproteins. The lipids, or fatty cholesterol components, are wrapped inside a water-soluble protein coat. Different types of lipoproteins contain varying lipoproteins from a dynamic economy within the body, transporting cholesterol to some tissues and removing it from others. The main cholesterol-carrying compound in the body is low-density lipoprotein, or LDL-cholesterol. LDL is often referred to as the "bad cholesterol" because it appears to play a key role in depositing cholesterol within arteries. It's called low-density because it has very little protein, the most dense contents of the molecule, and is composed mainly of fats. High levels of LDL are linked to an increased risk of coronary heart disease. High-density lipoprotein, or HDL, is often termed "good cholesterol" because it appears to help remove cholesterol from artery walls and transport it to the liver for excretion. In contrast to LDL cholesterol, low levels of HDL are associated with an increased risk of coronary heart disease, while higher levels of HDL appear to protect against the disease.

Other subtypes of cholesterol particles include chylomicrons, which are produced by intestinal cells when fat is digested, and very-low-density lipoprotein (VLDL), manufactured by the liver as an important precursor of LDL cholesterol production. VLDL is the major lipoprotein that transports the triglycerides produced by the liver.

For the purpose of determining heart disease risk, LDL and HDL are key.

Given all the evidence that high-fat, high-cholesterol diets contribute to elevated levels of cholesterol in the blood, and that high blood cholesterol is a definite risk factor for heart disease, it might seem natural to assume that lowering blood cholesterol, by diet or other means, will reduce that risk.

It is an objective of the invention to provide a method of isolating a protein which is involved in intestinal cholesterol absorption and is the molecular protein target for cholesterol absorption inhibitors. Such a method is deemed to contribute large benefit for therapeutic efforts to control elevated cholesterol levels.

The invention relates to a method for isolating a protein wherein a] biological material is provided, b] the biological material from a] is incubated with a photo-reactive 2-azetidinone compound which is radioactively labeled and which is able to specifically bind to said protein, c] the biological material is solubilized and the cell debris are removed, d] the supernatant is added onto a device harboring wheat germ lectin agarose, e] the eluat of the wheat germ lectin agarose from d] is applied to a hydroxylapatite column, which is eluted by means of a phosphate buffer gradient f] the radioactively labeled fractions from e] are loaded onto a preparative SDS-PAGE, g] the radioactively labeled fractions are collected and possibly precipitated.

The biological material is taken preferably from intestinal tissue or cells from an intestinal cell culture or ideal brush border cells from a human, a rat, a mouse or a rabbit.

The photoreactive 2-azetidinone compounds have preferably the following structure (Kramer, W. et al. (2000) FEBS Letters 487, 293-297)

Formula I wherein R shall be selected from one of the following groups a) to e):

a)

—CH₂NH—CO—CH₃ b)

c)

d)

e)

The synthesis of compounds of the formula I a, b and c has been disclosed in DE 10042447 A1 which was published at 28 Mar. 2002. Synthesis of compounds of formula I d and e is described in the examples hereinafter.

A photolabile group in a molecule can be used to produce covalent linkages to a molecule, preferably a protein, located in the direct vicinity. For this purpose, the compound with the photolabile group is initially brought into the direct vicinity of the molecule to which the covalent connection is to be produced. This can take place, for example, through another part of the compound which acts as a specific inhibitor of a protein, preferably an inhibitor of cholesterol absorption. Contacting the compound with the molecule is followed by irradiation with UV light. The irradiation with UV light activates the photolabile group and initiates the production of a covalent connection to the interacting molecule, in particular to a protein. Suitable as photolabile group are, for example, diazirine, azido or carbonyl functional groups.

It is possible to employ for the irradiation a conventional UV lamp like that used, for example, for visualizing polynucleotides with intercalated ethidium bromide or for sterilizing laboratory surfaces, or a photochemical reactor obtainable inter alia from "The Southern Ultraviolet Company, Hamden, Conn.". The disruption of the cells after irradiation with UV light is carried out using conventional methods. Examples thereof are repeated freezing and thawing, treatment of the cells with ultrasound, the use of a French press or the addition of a detergent and enzymes. The fractionation of the proteins of the cell lysate can be carried out, for example, by precipitation with ammonium sulfate, by differential centrifugation or application of chromatographic techniques. Chromatographic techniques suitable for this purpose are, for example, denaturing or nondenaturing polyacrylamide gel electrophoresis in one or two dimensions, high pressure liquid chromatography, ion exchange chromatography or affinity chromatography. These techniques are familiar to the skilled worker and are dealt with in detail for example in "Current Protocols in Protein Science"; John E. Caligan; Ben M. Dunn; Hidde L. Ploegh; David W. Speicher; Paul T. Wingfield; Wiley and Sons; ISBNO-471-11184-8.

Preferably, the detection of a protein after a fractionation takes place by means of the radiolabeling of the compound containing an inhibitor of intestinal cholesterol absorption and a photolabile group. A radioactive isotope which can be used for this purpose is, for example, $^3$H or $^{14}$C. A suitable detection method is, for example, detection of the protein which contains a covalently bonded compound by means of a film material used for X-ray photography after the protein has been introduced onto a polyacrylamide gel with the aid of polyacrylamide gel electrophoresis. Other suitable detection methods are liquid scintillation counting or flat bed scanning.

Biological material consists preferably of intestinal cells. The intestinal cells can be provided, for example, by dissection of the intestine from animals and subsequent purification, enzymatic disruption of the connective tissue and suspension of single cells in isotonic buffer solutions. Intestinal tissues suitable for the provision of intestinal cells are, inter alia, the corresponding parts of animals remaining after slaughtering. Intestinal cells can also be provided from human intestinal tissue after parts of the intestine have been obtained at operation. The intestinal cells can also consist of intestinal cell cultures provided for the purpose of the invention by application of cell culture techniques. Parts of intestinal cells may be organelles of the intestinal cells. Organelles are, preferably, membranes of the intestinal cells. Membranes of the intestinal cells can be obtained by differential centrifugation after disruption of these cells. Parts of intestinal cells are, preferably, also protein fractions. Provision of intestinal cells or parts of intestinal cells are intestinal cells consist preferably of cells from the brush border of the intestinal tissue of mammalian organisms.

Mammalian organisms from which these intestinal cells are obtained preferably include, but are not limited to humans, monkeys, cattle, pigs, rats, mice, rabbits, hamsters or other vertebrate species. These cells may be provided by preparing cell suspensions from the brush border tissue of the intestine of such organisms. Suitable intestinal material is obtained, for example, by surgical procedures. Other sources may derive from the parts of animals remaining after slaughtering. Cells of an intestinal cell line are equally suitable. To prepare suitable cell preparations, the intestinal tissue may be subjected to an enzyme treatment to release single cells and then undergo differential centrifugation. The resulting cells or organelles are subsequently taken up in suitable aqueous media. These aqueous media may contain buffer substances, salts, proteins and, in addition, excipients.

The invention relates also to a method for isolating a binding protein for cholesterol absorption inhibitors being involved in intestinal cholesterol absorption wherein a] biological material is provided, b] the biological material from a] is incubated with a photoreactive inhibitor of cholesterol uptake which is radioactively labeled or which is biotin-tagged.

c] the biological material from b] is solubilized and the cell debris are removed, d] the supernatant is submitted to chromatographic procedures or is added onto streptavidin-agarose, e] the eluat is added onto a SDS-PAGE, f] proteins running in a size range of 140 to 150 kDa excised, eluted and possibly refolded.

The biological material is taken preferably from intestinal tissue or cells from an intestinal cell culture or ideal brush border cells from a human, a rat, a mouse or a rabbit.

The inhibitor of cholesterol uptake which is biotin tagged has preferably the structure:

The invention refers also to a protein with ability to specifically bind cholesterol absorption inhibitors which has been isolated by a method of the invention as aforementioned. The protein has preferably a size of 140 to 150 kDa and most preferably a size of 145 kDa. The protein is possibly glycosylated.

The molecular weight of the proteins are stated subject to a certain range of uncertainty which is caused by the SDS polyacrylamide gel electrophoresis method used, but is also known for other corresponding methods. The variations in the molecular weights are in the region of up to +/−10%. The stated values represent the means of a plurality of experiments. In the case of the protein with the stated molecular weight of 145 kDa, the determinations of the molecular weight in 10 experiments carried out independently of one another by SDS polyacrylamide gel electrophoresis resulted in a mean of 145.3 kDa with a standard deviation of +/−7.55 kDa.

Details of suitable methods for checking glycosylation are to be found by the skilled worker in "Carbohydrate Biotechnology Protocols, Methods in Biotechnology, 10 (1999) Humana Press, ISBN 0-89603-563-8, Editor C. Bucke".

The invention refers furthermore to a complex formed by a protein of the invention and a compound having the following structure The invention refers furthermore to a pharmaceutical composition comprising a protein of the invention and pharmaceutically acceptable compounds and/or excipients for formulation of a medicament. Such substances are commonly known and described, for example, in Remingtons Pharmaceutical Sciences, fifth edition, by Mack Publishing Company.

The invention refers also to a pharmaceutical composition comprising a complex of a protein of the invention and a compound as aforementioned as well as pharmaceutically acceptable compounds for formulation of a medicament.

The invention includes also use of a protein of the invention for manufacturing of a pharmaceutical composition for treatment of a disease which is linked to elevated cholesterol-levels. Such diseases are, for example, obesitas, arteriosclerosis, high blood pressure, heart failure and others. A cholesterol level of 199 mg/dL is considered to be elevated.

The invention includes also the use of a complex of a protein of the invention and a compound as aforementioned for manufacturing of a pharmaceutical composition for treatment of a disease which is linked to elevated cholesterol-levels.

The invention also refers to use of a protein of the invention for identifying a compound which inhibits cholesterol reuptake wherein
a] biological material is provided which contains the protein of the invention,
b] a compound is provided,
c] the biological material and the compound are brought in contact,
d] the amount of cholesterol taken up by the biological material from c] is determined,
e] the result from d] is compared with results from a control experiment wherein the cholesterol uptake is determined from biological material which has the same species and/or tissue specificity as the biological material from a] but was not brought in contact with a compound of b],
f] the results from e] are indicating a compound which inhibits cholesterol reuptake when diminished cholesterol uptake from cells which have been brought in contact with a compound from b] is determined.

The invention refers also to a medicament comprising a compound which is identified by such a method as well as pharmaceutically acceptable expedients for treatment of a disease which is linked to elevated cholesterol levels.

The molecular weight of such a compound is preferably in a range of 100 to 50 000 Da and more preferably between 100 and 5000 Da. This compound could be a cholesterol analogue, a protein a peptide or a fatty acid containing compound.

The providing of a compound takes place, for example, by chemical synthesis. The compound may be part of a collection of chemical compounds like those resulting from storage and cataloging of the chemical compounds from completed synthesis programs ("compound libraries"). The compound may in other cases have been produced by a microorganism, in particular a bacterium, a fungus or an animal or plant species (natural substances). In the case of a natural substances, the providing can also take place by isolation from the appropriate organisms. The contacting of a protein with a compound takes place in most cases in aqueous solutions to which a certain proportion of a solvent such as, for example, dimethyl sulfoxide or ethanol has be admixed. The aqueous solutions may contain also buffer substances, ions or stabilizing additions such as proteins, glycerol or others. Particular constant conditions, for example for the temperature, the pH, the ionic conditions, the concentration of the protein or of the compound, or of the volume, may be advantageous for the contacting. Thus, for example, it may be preferable to keep the temperature constant at 37° C. during the contacting. The determination of the binding of the compound to the protein after carrying out the contacting takes place, for example, by interaction with cholesterol or cholesterol adsorption inhibitors which are radiolabeled in another way, using the displacement of the cholesterol or cholesterol absorption inhibitors as a measure of the affinity of the compound for the protein.

EXAMPLES

Synthesis of 5-(2-Oxo-hexahydro-thieno[3,4-d]imidazol-6-yl)-pentanoic acid[2-(4-azido-phenyl)-1-(4-{4-[3-(3-hydroxy-3-phenyl-propyl)-2-(4-methoxy-phenyl)-4-oxo-azetidin-1-yl]-phenylcarbamoyl}-butylcarbamoyl)-ethyl]amid The number 1 to 14 within the following passage refer to the general reaction scheme of FIG. 1

Synthesis of the Biotin-Tagged Photoreactive Cholesterol Inhibitor (5-(2-Oxo-hexahydro-thieno[3,4-d]imidazol-6-yl)-pentanoic acid[2-(4-azido-phenyl)-1-(4-{4-[3-(3-hydroxy-3-phenyl-propyl)-2-(4-methoxy-phenyl)-4-oxo-azetidin-1-yl]-phenylcarbamoyl}-butylcarbamoyl)-ethyl]-amid)

Figure 2:
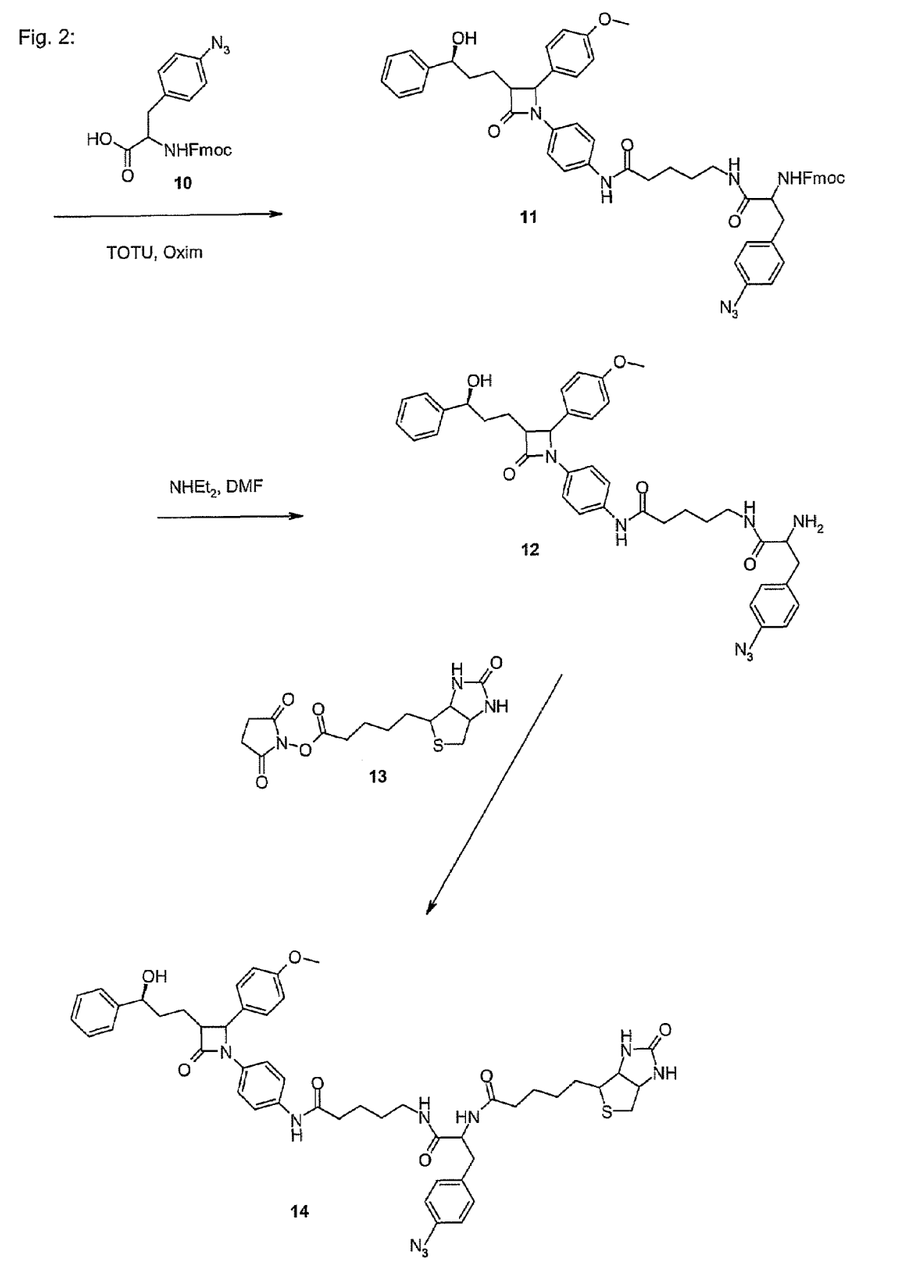
FIG. 2: Part 2 of reaction scheme for synthesis of 5-(2-Oxo-hexahydro-thieno[3,4-d]imidazol-6-yl)-pentansäure[2-(4-azido-phenyl)-1-(4-{4-[3-(3-hydroxy-3-phenyl-propyl)-2-(4-methoxy-phenyl)-4-oxo-azetidin-1-yl]-phenylcarbamoyl}-butylcarbamoyl)-ethyl]amid (14).

The numbers 1 to 14 within the following passage concerning synthesis of said biotin-tagged photoreactive cholesterol inhibitor refers to the reaction scheme of FIG. 1 and FIG. 2.

3-[5-(tert-Butyl-dimethyl-silanyloxy)-5-phenyl-pentanoyl]-4-phenyl-oxazolidin-2-on (1)

30 g of 3-(5-Hydroxy-5-phenyl-pentanoyl)-4-phenyl-oxazolidin-2-on are solved in 50 ml of DMF. After addition of 14.3 g of imidazol and 19 g of tert.-Butyl-dimethylsilylchlorid in 25 ml of DMF the reaction is stirred at room temperature until all components are dissolved (2-4 h). The reaction solution is evaporated, and after water was added extracted by acetic acid ethylester. After drying of the organic phase by magnesium sulfate and evaporation compound 1 is obtained: $C_{26}H_{35}NO_4Si$ (453.6) MS (ESI$^+$) 476 (M+Na$^+$).

(4-Methoxy-benzylidene)-(4-nitro-phenyl)-amin (2)

To 50 g (370 mmol) of anisaldehyd in 160 ml of isopropanol 51 g (370 mmol) of para-nitroanilin are added. After 2 h at 80° C. the product precipitates. The reaction mixture cooled to room temperature and filtered. The residue is washed with isopropanol. After drying 62.9 g of product 2 is obtained (yield of 66%) in form of yellow crystals: $C_{14}H_{13}N_2O_3$ (257.27).

3-{5-(tert-Butyl-dimethyl-silanyloxy)-2-[(4-methoxy-phenyl)-(4-nitro-phenylamino)-methyl]-5-phenyl-pentanoyl}-4-phenyl-oxazolidin-2-on (3)

To 5.4 g (12.0 mmol) of product 1 and 6.2 g (24 mmol) of product 2 in 135 ml of methylenehloride 8 ml of diisopropylethylamine is added at 10° C. and 4.8 ml of trimethylsilylchloride is added dropwise. After 1 h 14 ml of a 1 molar solution of titantetrachloride in methylenehloride is added dropwise at −10° C. It is stirred for 3 h at −10° C. and further 12 h at −30° C. stored without stirring. Afterwards 8 ml of acetic acid and 140 ml of a 7% aqueous solution of tartratic acid is added and it is stirred for further 2 h at room temperature. After addition of 50 ml of a 20% aqueous solution of sodiumhydrogensulfit it is stirred for another 1 h and extracted with methylenehloride. The organic phase is dried by magnesium sulfate, evaporated and purified by chromatography on silica gel/Ethylacetate/heptane=1/3->1/1. 6.3 g (74%) of product 3 is obtained in form of a light yellow solid compound: $C_{40}H_{47}N_3O_7Si$ (709.92) MS (ESI$^+$) 710 (M+H$^+$).

3-[3-(tert-Butyl-dimethyl-silanyloxy)-3-phenyl-propyl]-4-(3-methoxy-phenyl)-1-(4-nitro-phenyl)-azetidin-2-on (4)

A mixture comprising 6.1 g (8.6 mmol) of product 3, 7.3 ml of bistrimethylsilylacetamid, 0.5 g of Tetrabutylammoniumfluorid and 100 ml of tert-butylmethylether is stirred under a argon atmosphere for 10 h at room temperature. After finishing of the reaction 5 ml of acetic acid are added slowly by cooling with ice and evaporated. The residue is separated by chromatography on silica gel (ethylacetate/heptane=1/2). 3.3 g (70%) of product 4 is obtained in form of a light yellow compound in solid form: $C_{31}H_{38}N_2O_5Si$ (546.74) MS (ESI$^+$) 547.3 (M+H$^+$).

1-(4-Amino-phenyl)-3-[3-(tert-butyl-dimethyl-silanyloxy)-3-phenyl-propyl]-4-(3-methoxy-phenyl)-azetidin-2-on (5)

A reaction is performed with 3.0 g (5.5 mmol) of product 4 in 50 ml ethylacetate and 1.0 g of palladium charcoal 10% for 2 h at 5 bar of a hydrogen atmosphere using an autoclave. The reaction solution is filtrated, evaporated and separated by chromatography on silica gel (methylenehloride/methanol=10/1). 2.4 g (86%) of product 5 is obtained in form of a colourless compound in solid form: $C_{31}H_{40}N_2O_3Si$ (516.76) MS (ESI$^+$) 517.4 (M+H$^+$).

1-(4-Amino-phenyl)-3-(3-hydroxy-3-phenyl-propyl)-4-(3-methoxy-phenyl)-azetidin-2-on (6)

15 ml of 2N aqueous hydrochloric acid are added to 2.3 g of product 5 in 20 ml of tetrahydrofuran and stirred for 2 h. An aqueous solution of sodium hydrogencarbonate is added to the reaction and extracted by ethylacetate. The organic phase is dried by magnesium sulfate, evaporated and purified by chromatography on silica gel (ethylacetate/heptane=1/1->1/0). 1.1 g of product 6 is obtained in form of a colorless compound in solid form: $C_{25}H_{26}N_2O_3$ (402.50) MS (ESI$^+$) 403.2 (M+H$^+$).

13

(4-{4-[3-(3-Hydroxy-3-phenyl-propyl)-2-(4-methoxy-phenyl)-4-oxo-azetidin-1-yl]-phenylcarbamoyl}-butyl)-carbamioic acid-9H-fluoren-9-ylmethyl ester (8)

.8 g (2.0 mmol) of product 6 and 1.35 g (4.0 mmol) of 5-(Fmoc-amino)-valerianic acid 7 (Fluka) are solved in 15 ml of DMF (dimethylformamide). Stepwise is added the following: 4.8 g of TOTU (Fluka), 1.6 g of Oxime (Hydroxyiminocyanouceti acid-ethylester; Fluka) and 5.5 ml of NEM (4-Ethyl-morpholin). After 1 h at room temperature the reaction is diluted with 100 ml of ethylacetate and washed for three times with water. The organic phase is dried by $MgSO_4$, filtrated and evaporated. The residue is purified by flash chromatography (ethylacetate/n-heptane 2:1). 0.58 g (41%) of product 8 is obtained in form of a amorphic solid compound: $C_{45}H_{45}N_3O_6$ (723.8) MS (ESI$^+$) 724.4 (M+H$^+$).

14

5-Amino-pentanoic acid-{4-[3-(3-hydroxy-3-phenyl-propyl)-2-(4-methoxy-phenyl)-4-oxo-azetidin-1-yl]-phenyl}-amide (9)

570 mg (0.78 mmol) of product 8 and 0.8 ml of diethylamine are solved in 5 ml of DMF (dimethylformamide). It is evaporated after 1 h at room temperature. The residue is purified by flash chromatography (methylenechloride/methanol/conc. ammoniac 30:10:3) 220 mg (56%) of product 9 is obtained in form of an amorphic solid compound: $C_{30}H_{35}N_3O_4$ (501.63) MS (ESI$^+$) 502.3 (M+H$^+$).

[2-(4-Azido-phenyl)-1-(4-{4-[3-(3-hydroxy-3-phenyl-propyl)-2-(4-methoxy-phenyl)-4-oxo-azetidin-1-yl]-phenylcarbamoyl}-butylcarbamoyl)-ethyl]-carbamoic acid-9H-fluoren-9-ylmethyl ester (11)

200 mg (0.40 mmol) of product 9 and 340 mg (0.79 mmol) of Fmoc-p-azido-Phe-OH 10 (Bachem) are solved in 4 ml DMF (dimethylformamide) and reacted according to production of product 8. 300 mg (82%) of product 11 is obtained in form of an amorphic solid compound: $C_{54}H_{53}N_7O_7$ (912.07) MS (ESI$^+$) 912.5 (M+H$^+$).

300 mg (0.33 mmol) of product 11 and 0.8 ml of diethylamine are solved in 4 ml DMF (dimethylformamide) and reacted according to production of compound 9. 42 mg (19%) of compound 12 is obtained in form of an amorphic solid compound: $C_{39}H_{43}N_7O_5$ (689.82) MS (ESI$^+$) 690.3 (M+H$^+$).

5-[2-Amino-3-(4-azido-phenyl)-propionylamino]-pentanoic acid{4-[3-(3-hydroxy-3-phenyl-propyl)-2-(4-methoxy-phenyl)-4-oxo-azetidin-1-yl]-phenyl}-amid (12)

12

5-(2-Oxo-hexahydro-thieno[3,4-d]imidazol-6-yl)-pentanoic acid-[2-(4-azido-phenyl)-1-(4-{4-[3-(3-hydroxy-3-phenyl-propyl)-2-(4-methoxy-phenyl)-4-oxo-azetidin-1-yl]-phenylcarbamoyl}-butylcarbamoyl)-ethyl]-amid (14)

14

40 mg (0.058 mmol) of compound 12 and 60 mg of D-biotinyl-N-hydroxysuccinimide 13 (Bachem) are solved in 0.5 ml DMF (dimethylformamide). It is evaporated after 1 h at room temperature. The residue is purified by flash chromatography (methylenchloride/methanol/conc. ammonia 30:5:1). 29 mg (55%) of compound 14 is obtained in form of an amorphic solid compound: $C_{49}H_{57}N_9O_7S$ (912.12) MS (ESI$^+$) 916.6 (M+H$^+$).

Photoaffinity Labeling and Binding Studies:

Vesicles from the brush border tissue of the small intestine of rabbits were isolated by methods known to the skilled worker (Kramer et al. J. Biol. Chem. 268, 18035-18046 (1993)). The photoaffinity labeling using a radiolabeled compound of the Formula I a), or Formula I b) or, Formula I c), or Formula I d), or Formula I e) of this invention was carried out in a photochemical reactor of the Rayonet RPR-100 type (obtainable from "The Southern Ultraviolet Company, Hamden, Conn."). The brush border membrane vesicles thereof (100 to 200 μg of protein) were incubated with one of the compounds in a volume of 200 μl in 10 mM Tris/Hepes buffer (pH 7.4), 100 mM NaCl, 100 mM mannitol at 20° C. in the dark for 5 min. In place of the brush border vesicles it is also possible to use organelles, in particular membranes thereof. The statements hereinafter apply correspondingly to these. The incubation in the dark was followed by irradiation with UV light of 254 nm for 20 seconds or 60 seconds. The brush border vesicles were then washed twice with the buffer mentioned. The proteins were precipitated by conventional techniques such as, for example, addition of ethanol, addition of a salt or detergent, heating, repeated freezing and thawing, or another suitable method known to the skilled worker, and fractionated by SDS polyacrylamide gel electrophoresis. The radiolabeled proteins were detectable by LSC or fluorography. The affinity of the labeled proteins from the brush border tissue for the compounds was in the range from 1 to 100 nM.

Animals and Membrane Preparations:

Male New Zealand white rabbits weighing 4-5 kg (Harlem Winkelmann, Borchem, Germany) were kept on Altronin® standard diet C 2023 (Altronin®, Lage, Germany) ad libitum. Brush border membrane vesicles from the stomach, duodenum, jejunum, ileum, cecum, colon, rectum and kidney were prepared by the $Mg^{2+}$-precipitation method. Rat liver microsomes and rat adipocyte membranes were prepared according to standard techniques.

Inhibition of Cholesterol Absorption:

Intestinal cholesterol absorption was determined by a modification of the Zilversmit/Hughes method. Male NMRI mice (Charles River Deutschland GmbH, Salzfeld, Germany) kept on regular chow (Altronin®, Lage, Germany) were starved for 12 h. 0.5 ml of a solution of 0.5% methylcellulose/5% Solutol (BASF, Ludwigshafen, Germany) as vehicle with or without 3 mg of the respective cholesterol absorption inhibitor were applied by gavage to each animal followed by 0.25 ml of Intralipid® (Pharmacia & Upjohn, Erlangen, Germany) solution containing 0.24 μCi [$^{14}C$]cholesterol and 0.25 μCi [$^3H$]sitosterol. The animals (five mice per group) were kept on metabolism cages and feces were collected. After 24 h the animals were killed and the radioactivity in the feces and the liver was determined by combustion analysis.

Solubilization of the 145 kDa Binding Protein for Cholesterol Absorption Inhibitors:

Rabbit small intestinal brush border membrane vesicles were washed several times with 10 mM Tris/Hepes buffer (pH 7.4)/300 mM mannitol after photoaffinity labeling. The resulting pellet was solubilized at a protein concentration of 1 mg/ml for 60 min at 4° C. in 10 mM Tris/Hepes buffer (pH 7.4)/75 mM KCl/5 mM $MgCl_2$/1 mM EGTA/1 mM DTT/1% (w/v) n-octylglucoside/1% Triton X-100/1% (w/v) ("solubilization buffer"). Alternatively, membrane proteins could be solubilized at a protein concentration of 10 mg/ml with 1% SDS in 10 mM Tris/Hepes buffer (pH 7.4) at 4° C. for 10 min followed by a 1:10 dilution with 10 mM Tris/Hepes buffer (pH 7.4)/1% n-octylglucoside. After centrifugation, the supernatants containing solubilized membrane proteins were mixed and diluted with the appropriate buffers for chromatography, containing 1% n-octylglucoside as detergent.

Purification of the Radiolabeled 145 kDa Binding Protein for Cholesterol Absorption Inhibitors after Photoaffinity Labeling with the Photoreactive 2-Azetidinone C-1:

Photoaffinity Labeling

8 Samples of rabbit ileal brush border membrane vesicles (250 μg of protein) were incubated with 66 nM (0.3 μCi) of [$^3H$]C-1 in 10 mM Tris/Hepes buffer (pH 7.4)/100 mM NaCl/100 mM mannitol for 30 min at 20° C. in the dark. After irradiation for 30 sec at 254 nm in a Rayonet RPR 100 photochemical reactor equipped with 4 RPR 2537 Å lamps (The Southern Ultraviolet Company, Hamden, Conn., USA) the samples were collected and after centrifugation the membrane vesicles were resuspended in 2 ml 10 mM Tris/Hepes buffer (pH 7.4)/300 mM mannitol and centrifugated after 20 min at 20° C. This procedure was repeated three times. The resulting pellet was solubilized with 2 ml "solubilization buffer". After centrifugation, a 40 μl aliquot of the supernatant was removed and analyzed by SDS PAGE and subsequent slicing of the gel for incorporation of radioactivity into membrane proteins.

Wheat-Germ Lectin Affinity Chromatography

The supernatant containing solubilized membrane proteins were added to 0.5 ml of wheat germ lectin agarose gel. After 30 min at 20° C. the beads were collected by centrifugation and washed 3 times with 2 ml of 10 mM Tris/Hepes buffer (pH 7.4)/100 mM NaCl/100 mM mannitol/1% (w/v) n-octylglucoside. Adsorbed proteins were eluted with 4 portions of 2 ml of 10 mM Tris/Hepes buffer (pH 7.4)/100 mM NaCl/100 mM mannitol/300 mM N-acetyl-D-glucoseamine; in all eluates the activities of aminopeptidase N and sucrase were measured and from 100 μl aliquots of each fraction protein was precipitated and analyzed by SDS-PAGE.

Hydroxylapatite Chromatography

The N-acetylglucoseamine eluates of the wheat germ lectin chromatography were diluted tenfold with 10 mM sodium phosphate buffer (pH 7.4)/1% (w/v) n-octylglucoside and applied to a hydroxylapatite column (10 cm height, 1 cm diameter) equilibrated with 10 mM sodium phosphate buffer (pH 7.4)/1% (w/v) n-octylglucoside at a rate constant of 0.25 ml/min and collection of 1 ml fractions. Subsequently proteins were eluted as follows: 10 ml 10 mM sodium phosphate buffer (pH 7.4)/1% (w/v) n-octylglucoside followed by the following phosphate gradients: 15 ml with 10 to 250 mM, 15 ml with 250 to 700 mM and 10 ml with 700 to 1000 mM phosphate. In each fraction the activity of aminopeptidase N and sucrase and radioactivity was determined. From each fraction 100 μl were removed and protein was precipitated followed by SDS-PAGE with consequent determination of the distribution of radioactively labeled proteins by slicing of the gels into 2 mm pieces.

Preparative SDS Gel Electrophoresis

The fractions containing the radioactively labeled 145 kDa protein were collected and protein was precipitated with chloroform/methanol. After dissolution in SDS-sample buffer (62.5 mM Tris/HCl (pH 6.8) 2% SDS/5%/2-mercaptoethanol/10% glycerol/0.001% bromophenol blue the sample was centrifuged and the clear supernatant was applied to the separation gel of a preparative 7.5% SDS gel (diameter 28 mm; length of separation gel: 5 cm). Electrophoresis was performed at 500 V (40 mM, 6 W) and the eluate was fractionated into 1.5 ml fractions. 150 μl-Aliquots of each fraction were used for analysis of protein composition by SDS-PAGE.

Purification of the 145 kDa-Binding Protein for Cholesterol Absorption Inhibitors by Streptavidin-Biotin Affinity Chromatography:

10 Samples of rabbit ileal brush border membrane vesicles (200 μg of protein) were incubated with 200 μM of the biotin-tagged cholesterol inhibitor C-4 in 10 mM Tris/Hepes buffer (pH 7.4)/100 mM NaCl/100 mM mannitol for 30 min in the dark at 20° C. followed by irradiation at 254 nm for 30 sec in a Rayonet RPR-100 photochemical reactor equipped with 4 RPR 2537 Å-lamps. After collecting, the vesicles were washed 3 times with 2 ml Tris/Hepes buffer (pH 7.4)/300 mM mannitol. The final pellet was suspended in 2 ml of "solubilization buffer" for 1 h at 4° C. After centrifugation, the clear supernatant was mixed with 0.5 ml of streptavidin-agarose beads and kept under stirring at 4° C. for 2 h. After centrifugation, the beads were incubated with 2 ml 10 mM Tris/Hepes buffer (pH 7.4)/300 mM mannitol/1% n-octylglucoside/4 mM PMSF/4 mM iodoacetamide/4 mM EDTA/for 10 min at 4° C. followed by centrifugation. After repeating this procedure twice, proteins were eluted from the streptavidin-agarose beads with 3 portions a 2 ml of the above buffer containing 5 mM biotin. From all eluates aliquots were removed for the determination of the enzymatic activity of aminopeptidase N and sucrase and for analysis by SDS-PAGE. For final purification the biotin eluates containing the covalently modified 145 kDa binding protein for cholesterol absorption inhibitors was achieved by preparative SDS gel electrophoresis as described above.

Enzymatic Fragmentation:

The 145 kDa protein isolated by both procedures was precipitated with chloroform/methanol and redissolved in 3 μl of Tris/HCl buffer (pH 6.8)/6.2% SDS/0.5% 2-mercaptoethanol/0.0005% bromophenol blue. Enzymatic fragmentation was performed by adding 5 μl of a freshly prepared solution of chymotrypsin (35 ng/ml) in the above buffer and incubation of 30° C. for 1 h. Reaction was stropped by addition of SDS sample buffer containing 4 mM EDTA/4 mM PMSF/4 mM iodoacetamide and heating for 5 min to 95° C. followed by subsequent SDS-PAGE on Tris/Tricine gels.

SDS Gel Electrophoresis

SDS-PAGE was carried out in vertical stab gels (20×17×0.15 cm) using an electrophoresis system LE 2/4 (Amersham Pharmacia Biotech, Freiburg, Germany) with gel concentrations of 7-10.5% at a ratio of 97.2% acrylamide and 2.8% N,N-methylene bisacrylamide or for analytical purposes in pre-casted NOVEX gels (4-12%, 12% or 15%, Invitrogen (Groningen, The Netherlands) using an electrophoresis system Xcell II from Novex. Electrophoretic separation of peptide fragments was performed in Tris/Tricine gels (16.5%) according to Schäggre & Jagow. After electrophoresis the gels were fixed in 12.5% trichloroacetic acid followed by staining with Serva Blue R 250. For determination of the distribution of radioactivity, individual gel lanes were cut into 2 mm pieces, protein was hydrolyzed with 250 μl of tissue solubilizer Biolute S and liquid scintillation counting using 4 ml of scintillator Quickszint 501.

Solubilization of the 145 kDa-Binding Protein for Cholesterol Absorption Inhibitors:

A prerequisite for purification of the 145 kDa-binding protein for cholesterol absorption inhibitors is a satisfactory solubilization of this integral membrane protein in a nondenaturated state. Solubilization experiments with a variety of detergents revealed that with SDS around 80-90% and with Zwittergent 9-13 about 60% of the photolabeled protein could be solubilized whereas with CHAPS, NP-40, digitonin and Triton-X-114 no significant solubilization could be achieved. 1%-solutions of nonionic detergents like Triton-X-100, n-octylglucoside, decylmaltoside, dodecylmaltoside or cholesterolhemisuccinate/dodecylmaltoside in 10 mM Tris/Hepes buffer (pH 7.4)/300 mM mannitol only led to partial solubilization of the 145 kDa protein thereby hampering its purification. Two protocols finally were found yielding 60-80% solubilization of the 145 kDa protein enabling a purification procedure: a) solubilization with 1% SDS with subsequent dilution with 1% n-octylglucoside to a starting concentration of 0.1% SDS/1% n-octylglucoside. b) solubilization with 10 mM Tris/Hepes buffer (pH 7.4)/75 mM KCl/5 mM $MgCl_2$/1 mM EGTA/1 mM DTT/1% Triton X-100/1% n-octylglucoside ("solubilization buffer"). The solubilization procedure allowed a successful fractionated of brush border membrane proteins by chromatography procedure.

Design of Biotin-Tagged 2-Azetidinone Photoaffinity Probe:

For a one-step purification of the target-protein for cholesterol absorption inhibitors we have coupled the biotin-containing photolabile group N-(biotinyl)-4-azidophenyl alanine via a spacer to the para-position of the N-phenyl or benzylamino ring of 2-azetidinone cholesterol absorption inhibitors. Structure activity relationship have demonstrated that this position allows considerable chemical modification maintaining the in vivo potency for inhibition of intestinal cholesterol absorption. After application of the biotin-tagged photoaffinity label C-4 to NMRI-mice intestinal cholesterol absorption was dose-dependently inhibited indicating a biological efficacy of the biotin-tagged photolabile cholesterol absorption inhibitor, a prerequisite for identification of the protein(s) being involved in intestinal cholesterol absorption by this probe. Photoaffinity labeling of rabbit small intestinal BBMV with the azidobenzoylderivative [$^3$H]C-1 in the presence of increasing concentrations of the biotin-tagged cholesterol inhibitor C-4 resulted in a concentration-dependent decrease in the extent of labeling of the 145 kDa-protein indicating a specific interaction of C-4 with the 145 kDa binding protein for cholesterol absorption inhibitors in the brush border membrane of small intestinal enterocytes.

Purification of the 145 kDa Binding Protein Photolabelled with the Tritium-Labeled 2-Azetidinone Cholesterol Absorption Inhibitor C-1:

The photolabeled 145 kDa-binding protein is localized in a molecular weight range where highly abundant membrane proteins of the brush border membranes like the sucrase/isomaltase complex or aminopeptidase N migrate on SDS-gels making therefore a complete separation from these proteins mandatory for sequence determination. The biochemical investigation identified the 145 kDa-protein as a glycosylated integrated membrane protein with a shift of molecular mass from 145 kDa to 110 kDa upon deglycosylation with N-glycanase. We therefore investigated various lectins as putative ligands for affinity chromatography. With wheat germ lectin agarose a complete retardation of the photolabeled 145 kDa protein was achieved whereas 70-80% of the enzymatic activity of sucrase and aminopeptidase N where eluted. With N-acetylglucoseamine the entire amount of the radiolabeled 145 kDa protein could be eluted together with 30-50% of aminopeptidase N and sucrase-activity. Overall, a 4-5 fold enrichment of the 145 kDa binding protein for cholesterol absorption inhibitors was achieved. For a further purification a number of different procedures were evaluated. Ion-exchange chromatography on Mono Q or Mono S columns led to a complete separation from sucrase/isomaltase but only partially from aminopeptidase N whereas with metal-chelating-affinity-chromatography no clear separation could be achieved. With hydroxylapatite chromatography a strong enrichment of the 145 kDa protein and separation from sucrase and aminopeptidase N could be achieved. An optimized phosphate gradient profile led to a nearly complete separation of the 145 kDa-protein from other membrane proteins; the 145 kDa protein was eluted at high phosphate concentrations and was devoid of significant enzymatic activities of sucrase or aminopeptidase N. Final purification was achieved by preparative SDS-PAGE of the eluates from hydroxylapatite chromatography. The estimated amount of pure 145 kDa protein was 1-3% of the material applied to the hydroxylapatite column indicating that an enrichment factor>150<500-fold with respect to brush border membranes and 2500-10 000 fold with respect to enterocyte total protein was achieved.

Purification of the 145 kDa Binding Protein for Cholesterol Absorption Inhibitors by Streptavidin-Biotin Affinity Chromatography after Photoaffinity Labeling with a Biotin-Tagged Photolabile Cholesterol Absorption Inhibitor

Rabbit small intestinal BBMV were incubated with 200 μM of C-4 and crosslinking was achieved by ultraviolet irradiation at 254 nm. After solubilization the covalently modified proteins containing the biotin-tagged 2-azetidinone cholesterol absorption inhibitors were extracted with streptavidin-beads. After intensive washing bound proteins were eluted with a 10 mM solution of biotin and analyzed by SDS-PAGE. Predominantly one protein of Mr 145 kDa was retained by the streptavidin-beads whereas no proteins were detectable if ultraviolet irradiation was omitted indicating that a 145 kDa protein is the primary binding protein for the biotin-tagged photolabile cholesterol absorption inhibitor C-4. The biotin-extracts from streptavidin-beads did not contain detectable enzymatic activities of sucrase/isomaltase or aminopeptidase N indicating that the eluted 145 kDa protein probably represents one single protein moiety modified by covalent binding of the biotin-tagged cholesterol absorption inhibitor. The presence of 200 μM of other cholesterol absorption inhibitors like ezetimibe during photolabeling with C-4 reduced the amount of 145 kDa protein extractable with streptavidin beads indicating a direct competition of cholesterol absorption inhibitors with C-4 for identical binding sites; in contrast, substrates for other intestinal nutrient transporters for bile acids, fatty acids, glucose, oligopeptides or amino acids did not influence the amount of extractable 145 kDa protein. Performing these labeling experiments with cell membranes from different organs revealed that only by labeling of BBMV from rabbit small intestine—duodenum, jejunum and ileum—a 145 kDa protein could be extracted whereas after labeling of BBMV from stomach, cecum, colon, rectum, kidney, liver or adipocytes no 145 kDa protein was retarded by streptavidin beads. Therefore, the 145 kDa binding protein could only be purified from those anatomical sites where intestinal cholesterol absorption occurs, the duodenum, jejunum and ileum. The 145 kDa protein purified by wheat germ lectin- and hydroxylapatite chromatography and by streptavidin-biotin-affinity chromatography are indistinguishable on SDS-gels. After enzymatic fragmentation with chymotrypsin nearly identical peptide patterns with a number of peptides in the molecular mass range of 4-35 kDa were obtained indicating that the 145 kDa proteins purified by both approaches are identical and contain predominantly if not exclusively one protein moiety only.

FIG. 1: Part 1 of reaction scheme for synthesis of 5-(2-Oxo-hexahydro-thieno[3,4-d]imidazol-6-yl)-pentansäure[2-(4-azido-phenyl)-1-(4-{4-[3-(3-hydroxy-3-phenyl-propyl)-2-(4-methoxy-phenyl)-4-oxo-azetidin-1-yl]-phenylcarbamoyl}-butylcarbamoyl)-ethyl]amid (14).

The invention claimed is:

1. A method for isolating a 145 kDa protein capable of specifically binding cholesterol absorption inhibitors, comprising the steps of:
    i) incubating mammalian intestinal tissue or cells with a photoreactive inhibitor of cholesterol uptake which is radioactively labeled and biotin-tagged,
    ii) solubilizing said intestinal cells and separating the supernatant from the cell debris,
    iii) adding said supernatant onto streptavidin-agarose,
    iv) adding the eluate of said streptavidin-agarose onto a SDS-PAGE and
    v) excising the proteins running in a size range of 140 to 150 kDa and eluting said proteins,
    vi) isolating a complex comprising the 145 kDa protein bound to the photoreactive inhibitor of cholesterol uptake and
    vii) separating the 145 kDa protein from the cholesterol absorption inhibitor,
    wherein the photoreactive inhibitor of cholesterol uptake which is biotin tagged has the following structure:

2. The method of claim 1 wherein said intestinal tissue or cells are from an intestinal cell culture or ileal brush border cells from human, rat, mouse or rabbit.

3. A method for isolating a complex formed by a purified 145 kDa protein capable of specifically binding cholesterol absorption inhibitors and a cholesterol absorption inhibitor, comprising the steps of:
    i) incubating mammalian intestinal tissue or cells with a cholesterol absorption inhibitor that is a photoreactive inhibitor of cholesterol uptake which is radioactively labeled and biotin-tagged,
    ii) solubilizing said intestinal cells and separating the supernatant from the cell debris,
    iii) adding said supernatant onto streptavidin-agarose,
    iv) adding the eluate of said streptavidin-agarose onto a SDS-PAGE and
    v) excising the proteins running in a size range of 140 to 150 kDa and eluting said proteins bound to said cholesterol absorption inhibitor , and
    iv) isolating the complex,
    said cholesterol absorption inhibitor having the following structure 4. A method for isolating a complex formed by a purified 145 kDa protein capable of specifically binding cholesterol absorption inhibitors and a cholesterol absorption inhibitor, comprising the steps of:
  i) incubating mammalian intestinal tissue or cells with a photoreactive inhibitor of cholesterol uptake which is biotin-tagged,
  ii) solubilizing said intestinal cells and separating the supernatant from the cell debris,
  iii) adding said supernatant onto streptavidin-agarose,
  iv) adding the eluate of said streptavidin-agarose onto a SDS-PAGE and
  v) excising the proteins running in a size range of 140 to 150 kDa and eluting said proteins bound to said cholesterol absorption inhibitor, and
  iv) isolating the complex,
  said photoreactive inhibitor having the following structure of Formula I:

Formula I wherein R shall be selected from one of the following groups a) and b):

* * * * *